United States Patent [19]

Ranade

[11] Patent Number: 5,684,009

[45] Date of Patent: *Nov. 4, 1997

[54] PARENTERAL SOLUTIONS CONTAINING 7-HALO-1,2,3,4-TETRAHYDRO-3-ARYL-6-QUINAZOLINE SULFONAMIDES

[75] Inventor: Vasant Ranade, Libertyville, Ill.

[73] Assignee: Academic Pharmaceuticals, Inc., Lake Bluff, Ill.

[*] Notice: The portion of the term of this patent subsequent to Feb. 13, 2015, has been disclaimed.

[21] Appl. No.: 299,493

[22] Filed: Sep. 1, 1994

[51] Int. Cl.$^6$ .......................... A61K 31/505; A61K 31/34
[52] U.S. Cl. ............................................. 514/259; 514/471
[58] Field of Search ...................................... 514/259, 471

[56] References Cited

U.S. PATENT DOCUMENTS 5,124,152  6/1992  Biringer et al. ......................... 424/422

Primary Examiner—William R. A. Jarvis
Attorney, Agent, or Firm—McDonnell Boehnen Hulbert & Berghoff

[57] ABSTRACT

Disclosed herein are parenteral solutions containing 7-halo-1,2,3,4-tetrahydro-3-aryl-6-quinazoline sulfonamides in Bis-Tris buffer useful in the treatment of hypertension, heart disease and heart failure and renal disease. Also disclosed are methods for preparing such solutions.

4 Claims, No Drawings

PARENTERAL SOLUTIONS CONTAINING 7-HALO-1,2,3,4-TETRAHYDRO-3-ARYL-6-QUINAZOLINE SULFONAMIDES

BACKGROUND OF THE INVENTION

1. Field of the Invention

The present invention relates to parenteral solutions containing 7-Halo-1,2,3,4-tetrahydro-3-aryl-6-qinazoline sulfonamides.

2. Description of the Related Art

Metolazone is a quinazoline diuretic approved for use in an oral tablet form (MYKROX®) for the treatment of hypertension, alone or in combination with other anti-hypertensive drugs of a different class. This compound acts primarily to inhibit sodium reabsorption at the cortical diluting site and to a lesser extent in the proximal convoluted tubule. Sodium and chloride ions are excluded in approximately equivalent amounts. The increased delivery of sodium to the distal-tubular exchange site results in increased potassium excretion.

To treat hypertension, the compound may be administered in oral dosage forms such as in the form of a tablet containing from 0.5–10 mg of metolazone, or it may be administered in the form of an intravenous solution.

Metolazone is also indicated for use in treating heart failure and renal disease. Further, when metolazone is combined with furosemide (lasix), the effectiveness of the diuretics is greatly enhanced. Furosemide can be administered intravenously to obtain the best and most rapid effect in emergencies. However, there is no intravenous formulation available of metolazone since metolazone is sparingly soluble in most solvents. Metolazone is only sparingly soluble in water, but is said to be somewhat more soluble in plasma, blood, alkali and organic solvents.

U.S. Pat. Nos. 3,360,518 and 3,557,111 disclose methods for preparing metolazone.

DESCRIPTION OF THE INVENTION

The present invention provides parenteral solutions comprising as an active ingredient a 7-Halo-1,2,3,4-tetrahydro-3-aryl-6-quinazoline sulfonamide of the following formula:

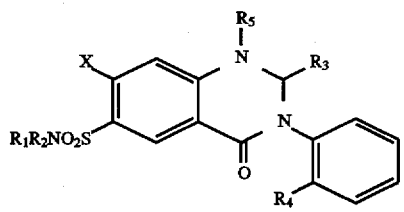

wherein X is a halogen;

$R_1$, $R_2$, $R_3$ and $R_4$ are independently selected from hydrogen and alkyl groups having from about 1 to 6 carbon atoms; and $R_5$ is hydrogen or an alkyl group having from about 1 to 6 carbon atoms.

More specifically, the present invention provides parenteral solutions suitable for intravenous administration containing as an active ingredient an effective anti-hypertensive amount of 7-chloro-1,2,3,4-tetrahydro-2-methyl-3-(-2-methylphenyl)-4-oxo-6-quinazoline sulfonamide in a sterile solvent comprising a [bis-(2-hydroxyethyl)-amino]tris-(hydroxymethyl)methane (Bis-Tris) buffer having a pH from about 10.5 to 12.5, and preferably from 11.5 to 12, i.e., metolazone-Bis-Tris solutions.

The invention further provides solutions having extended stability that are suitable for parenteral administration comprising metolazone in Bis-Tris buffer having a pH of from about 11.5 to 12.

Also included within the scope of the invention are methods for producing such solutions.

Still further, the invention provides solutions suitable for parenteral, e.g., intravenous, administration comprising an effective anti-hypertensive amount of metolazone in a Bis-Tris buffer having a pH of from about 11.5 to 12.

Yet further, the invention provides solutions suitable for parenteral administration comprising furosemide and metolazone in Bis-Tris buffer at a pH of from about 11.5 to about 12.

Further, the invention provides methods for treating an anti-hypertensive patient which comprises parenteral, e.g., intravenous, administraiton of an effective amount of a solution of metolazone in a Bis-Tris buffer.

Parenteral solutions comprising metolazone in Bis-Tris buffer according to the invention are typically prepared by mixing the required amount of metolazone, which may be purified prior to use, is mixed with the buffer and adding to the resulting solution sodium hydroxide or other suitable base until a pH of about 12 to 12.5 is reached. To this highly basic solution is then added a protic acid, such as, for example, acetic acid, preferably about 1 molar acetic acid, to adjust the pH of the solution to that at which metolazone is completely soluble. The process is preferably carried out at room temperature, although other temperatures are acceptable.

Most preferred solutions of metolazone and Bis-Tris buffer contain about 1 mg of metolazone per ml of solution. The concentration of Bis-Tris buffer in the solution is typically about 0.5M. The resulting solutions after cooling to room temperature may be sterilized by known means, e.g., ultra-filtration preferably a 13 mm, 0.45 micron filter, or ethylene oxide treatment and may be packaged into vials suitable for dispensing as parenteral products.

The preparation thus obtained at a pH of about 11.5 to 12 was found, quite unexpectedly, to remain in solution. The metolazone/Bis-Tris aqueous formulation demonstrates remarkable stability when stored at room temperature over at least a three week period without the formation of turbidity or precipitate.

The solution thus formulated is indicated for the treatment of hypertension, heart failure, or renal disease. Solutions may also be prepared in a similar manner to contain furosemide and metolazone. As with any potent drug, the dosage must be individualized by the treating clinician.

One skilled in the art will recognize that modifications may be made in the present invention without deviating from the spirit or scope of the invention. The invention is illustrated further by the following examples which are not to be construed as limiting the invention or scope of the specific procedures described herein.

EXAMPLE 1

To a mixture containing indicated quantities of metolazone (Research Biochemicals Inc., Lot # CC-1088E), cyclodextrine (American Maize Products Co.), and with or without polyvinyl pyrrolidones (Sigma Chemical Co.), in differing amounts, as well as a quantity (as indicated) of different buffers at different concentrations, were added. This mixture was stirred, and 5N NaOH solution was added dropwise until a clear solution resulted. The pH of this solution was generally between 12.0–12.5. (It was allowed to stand at room temperature for 30 minutes in cases where cyclodextrins were used). To this solution, 1M acetic acid was added in order to adjust to the desired pH at which the metolazone was completely soluble. The solution was filtered through 13 mm, 0.45 micron filter and stored in vials at room temperature and 40° C. for several days. The results of these experiments are reported in the following table.

METOLAZONE SOLUBILITY

| Buffer Used (0.1M unless otherwise stated) | Final conc. Metolazone mg/ml (mg/ml) | Final pH of Solution | Temp. for Storage | Observations on stability after standing for period of time* | | | | | | |
|---|---|---|---|---|---|---|---|---|---|---|
| | | | | 24 hr | 48 hr | 72 hr | 96 hr | 1 Wk | 2 Wk | 3 Wk |
| 12 ml Na Acetate + 0.1 ml Tween 80 | 1 | 6.7 | RT | ppt | | | | | | |
| 12 ml Na Acetate + 0.1 ml Tween 80 | 1 | 9.0 | RT | ppt | | | | | | |
| 12 ml Na Acetate + 0.2 ml Tween 80 | 1 | 6 | RT | ppt | | | | | | |
| 12 ml Na Acetate + 0.5 ml Tween 80 | 1 | 6 | RT | ppt | | | | | | |
| 12 ml Na Acetate + 2 ml Tween 80 | 1 | 9.5 | RT | ppt | | | | | | |
| 12 ml Na Acetate + 3 ml Tween 80 | 1 | 10.0 | RT | ppt | | | | | | |
| 12 ml Na Acetate + 2 ml AMPSO[1] | 1.0 with 66 mg β CD | 10.0 | RT | Clear | Clear | ppt | | | | |
| 12 ml Na Acetate + 2 ml Bicine[2] | 1.0 with 66 mg β CD | 10.0 | RT | Clear | Clear | ppt | | | | |
| 12 ml Na Acetate + 2 ml Bis-Tris | 1.0 with 66 mg β CD | 10.0 | RT | Clear | Clear | ppt | | | | |
| 12 ml Na Acetate + 2 ml CAPS[3] | 1.0 with 66 mg β CD | 10.0 | RT | Clear | Clear | ppt | | | | |
| 12 ml Na Acetate + 2 ml CHES[4] | 1.0 with 66 mg β CD | 10.0 | RT | Clear | Clear | ppt | | | | |
| 12 ml Na Acetate + 2 ml Glycine | 1.0 with 66 mg β CD | 10.0 | RT | Clear | Clear | ppt | | | | |
| 12 ml Na Acetate + 2 ml TAPS[5] | 1.0 with 66 mg β CD | 10.0 | RT | Clear | Clear | ppt | | | | |
| 12 ml Na Acetate + 2 ml Tricine | 1.0 with 66 mg β CD | 10.0 | RT | Clear | Clear | ppt | | | | |
| 12 ml Na Acetate + 2 ml TEA | 1.0 with 66 mg β CD | 10.0 | RT | Clear | Clear | ppt | | | | |
| 12 ml Na Acetate + 2 ml Tris | 1.0 with 66 mg β CD | 10.0 | RT | Clear | Clear | ppt | | | | |
| 5% NaHCO$_3$ | 1.5 | 11 | RT | ppt | | | | | | |
| AMPSO | 2 | 9.5 | RT | ppt | | | | | | |
| AMPSO | 2 | 10.0 | RT | ppt | | | | | | |
| AMPSO | 2 | 10.5 | RT | ppt | | | | | | |
| AMPSO | 1 | 10.0 | RT | ppt | | | | | | |
| AMPSO | 1.0 with 66 mg βCD | 10.0 | RT | Clear | ppt | | | | | |
| AMPSO | 1.0 | 12.0 | RT | ppt | ppt | ppt | ppt | ppt | → | |
| AMPSO | 1.0 | 12.0 | 40° | ppt | ppt | ppt | ppt | ppt | → | |

METOLAZONE SOLUBILITY

| Buffer Used (0.1M unless otherwise stated) | Final conc. Metolazone mg/ml (mg/ml) | Final pH of Solution | Temp. for Storage | Observations on stability after standing for period of time* | | | | | | |
|---|---|---|---|---|---|---|---|---|---|---|
| | | | | 24 hr | 48 hr | 72 hr | 96 hr | 1 Wk | 2 Wk | 3 Wk |
| AMPSO | 2.0 | 11.5 | RT | ppt | ppt | ppt | ppt | ppt | ppt | |
| AMPSO | 2.0 | 11.5 | 40° | ppt | ppt | ppt | ppt | ppt | ppt | |
| AMPSO | 2.0 | 12.0 | RT | ppt | ppt | ppt | ppt | ppt | ppt | |
| AMPSO | 2.0 | 12.0 | 40° | ppt | ppt | ppt | ppt | ppt | ppt | |
| Bicine | 2 | 9.5 | RT | ppt | | | | | | |
| Bicine | 2 | 10.0 | RT | ppt | | | | | | |
| Bicine | 2 | 10.5 | RT | ppt | | | | | | |
| Bicine | 1 | 10.0 | RT | ppt | | | | | | |
| Bicine | 1.0 with 66 mg βCD | 10.0 | RT | Clear | Clear | ppt | | | | |
| Bicine 0.05 | 1 | 11.5 | RT | ppt | ppt | ppt | ppt | ppt | | |
| Bicine 0.05 | 1 | 11.5 | 40° | ppt | | | | | | |
| Bicine 0.05 | 1 | 12.0 | RT | ppt | ppt | ppt | ppt | ppt | | |
| Bicine 0.05 | 1 | 12.0 | 40° | ppt | | | | | | |
| Bicine 0.05 | 2 | 11.5 | RT | ppt | ppt | ppt | ppt | ppt | ppt | |
| Bicine 0.05 | 2 | 11.5 | 40° | ppt | ppt | ppt | ppt | ppt | ppt | |
| Bicine 0.05 | 2 | 12.0 | RT | ppt | ppt | ppt | ppt | ppt | ppt | |
| Bicine 0.05 | 2 | 12.0 | 40° | ppt | ppt | ppt | ppt | ppt | ppt | |
| Bis-Tris | 1.5 | 10.4 | RT | ppt | | | | | | |
| Bis-Tris | 2 | 9.5 | RT | ppt | | | | | | |
| Bis-Tris | 2 | 10.0 | RT | ppt | | | | | | |
| Bis-Tris | 2 | 10.5 | RT | ppt | | | | | | |
| Bis-Tris | 1 | 10.0 | RT | ppt | | | | | | |
| Bis-Tris | 1.0 with 66 mg β CD | 10.0 | RT | Clear | Clear | ppt | | | | |
| Bis-Tris 0.05M | 1.0 | 11.5 | RT | Clear | Clear | Clear | Clear | → | | |
| Bis-Tris 0.05M | 1.0 | 11.5 | 40° | Clear | Clear | Clear | Clear | Clear | Clear | |
| Bis-Tris 0.05M | 1.0 | 12.0 | RT | Clear | Clear | Clear | Clear | Clear | Clear | |
| Bis-Tris 0.05M | 1.0 | 12.0 | 40° | Clear | → | | | | | |
| Bis-Tris 0.05M | 2.0 | 11.5 | RT | Clear | Clear | Clear | Clear | Clear | ppt | |
| Bis-Tris 0.05M | 2.0 | 11.5 | 40° | Clear | Clear | Clear | Clear | Clear | ppt | |
| Bis-Tris 0.05M | 2.0 | 12.0 | RT | Clear | Clear | Clear | Clear | Clear | ppt | |
| Bis-Tris 0.05M | 2.0 | 12.0 | 40° | Clear | Clear | Clear | Clear | Clear | ppt | |
| CAPS | 2 | 9.5 | RT | ppt | | | | | | |
| CAPS | 2 | 10.0 | RT | ppt | | | | | | |
| CAPS | 2 | 10.5 | RT | ppt | | | | | | |
| CAPS | 1 | 10.0 | RT | ppt | | | | | | |
| CAPS | 1.0 with 66 mg β CD | 10.0 | RT | Clear | Clear | ppt | | | | |
| CAPS | 1.5 | 11 | RT | ppt | | | | | | |
| CAPS | 1.5 | 10.4 | RT | ppt | | | | | | |
| CAPS 0.05 | 1.0 | 11.5 | RT | Clear | Clear | Clear | Clear | ppt | | |
| CAPS 0.05 | 1.0 | 11.5 | 40° | Clear | Clear | Clear | Clear | Clear | ppt | |
| CAPS 0.05 | 1.0 | 12.0 | RT | Clear | Clear | Clear | Clear | Clear | Clear | ppt |
| CAPS 0.05 | 1.0 | 12.0 | 40° | Clear | ppt | | | | | |
| CAPS 0.05 | 2.0 | 11.5 | RT | Clear | Clear | Clear | Clear | Clear | ppt | |
| CAPS 0.05 | 2.0 | 11.5 | 40° | Clear | Clear | Clear | Clear | Clear | ppt | |
| CAPS 0.05 | 2.0 | 12.0 | RT | Clear | Clear | Clear | Clear | Clear | ppt | |
| CAPS 0.05 | 2.0 | 12.0 | 40° | Clear | Clear | Clear | Clear | Clear | ppt | |
| CHES | 1 | 11.2 | RT | ppt | | | | | | |
| CHES | 1 | 10.8 | RT | ppt | | | | | | |
| CHES | 1 | 10.3 | RT | ppt | | | | | | |
| CHES | 1.5 | 10.4 | RT | ppt | | | | | | |
| CHES in D5W | 2 | 9.5 | RT | ppt | | | | | | |
| CHES in D5W | 2 | 10.0 | RT | ppt | | | | | | |
| CHES in D5W | 2 | 10.5 | RT | ppt | | | | | | |
| CHES in D5W | 1 | 10.0 | RT | ppt | | | | | | |
| CHES in D5W | 1.0 with 66 mg β CD | 10.0 | RT | Clear | Clear | ppt | | | | |
| CHES in D5W | 1 | 9.3 | RT | ppt | | | | | | |
| CHES in D5W 0.05 | 1 | 11.5 | RT | Clear | ppt | | | | | |
| CHES in D5W 0.05 | 1 | 11.5 | 40° | Clear | ppt | | | | | |
| CHES in D5W 0.05 | 1 | 12.0 | RT | Clear | ppt | | | | | |
| CHES in D5W 0.05 | 1 | 12.0 | 40° | Clear | ppt | | | | | |

-continued

METOLAZONE SOLUBILITY

| Buffer Used (0.1M unless otherwise stated) | Final conc. Metolazone mg/ml (mg/ml) | Final pH of Solution | Temp. for Storage | Observations on stability after standing for period of time* | | | | | | |
|---|---|---|---|---|---|---|---|---|---|---|
| | | | | 24 hr | 48 hr | 72 hr | 96 hr | 1 Wk | 2 Wk | 3 Wk |
| CHES in D5W 0.05 | 2 | 11.5 | RT | Clear | ppt | | | | | |
| CHES in D5W 0.05 | 2 | 11.5 | 40° | Clear | ppt | | | | | |
| CHES in D5W 0.05 | 2 | 12.0 | RT | Clear | ppt | | | | | |
| CHES in D5W 0.05 | 2 | 12.0 | 40° | Clear | ppt | | | | | |
| Glycine | 1 | 11.3 | RT | ppt | | | | | | |
| Glycine | 1 | 10.9 | RT | ppt | | | | | | |
| Glycine | 1 | 10.3 | RT | ppt | | | | | | |
| Glycine | 1.5 | 10.4 | RT | ppt | | | | | | |
| Glycine | 2 | 9.5 | RT | ppt | | | | | | |
| Glycine | 2 | 10.0 | RT | ppt | | | | | | |
| Glycine | 2 | 10.5 | RT | ppt | | | | | | |
| Glycine | 1 | 10.0 | RT | ppt | | | | | | |
| Glycine | 1.0 with 66 mg β CD | 10.0 | RT | Clear | Clear | ppt | | | | |
| $H_2O$ | 1 | 10.5 | RT | Clear | Clear | Color/ppt | | | | |
| $H_2O$ | 1 | 10.5 | 40° | Clear | Color/ppt | | | | | |
| $H_2O$ | 1 | 11.0 | RT | Clear | Clear | Color/ppt | | | | |
| $H_2O$ | 1 | 11.0 | 40° | Clear | ppt | | | | | |
| $H_2O$ | 2 | 10.5 | RT | Clear | Color | | | | | |
| $H_2O$ | 2 | 10.5 | 40° | Clear | ppt | | | | | |
| $H_2O$ | 2 | 11.0 | RT | Clear | Color/ppt | | | | | |
| $H_2O$ | 2 | 11.0 | 40° | Clear | ppt | | | | | |
| $H_2O$ | 1 | 11.0 | RT | Clear | Color/ppt | | | | | |
| $H_2O$ | 1 | 11.0 | 40° | Clear | Color/ppt | | | | | |
| $H_2O$ | 1 | 10.5 | RT | Clear | Color | | | | | |
| $H_2O$ | 1 | 10.5 | 40° | Clear | Color/ppt | | | | | |
| $H_2O$ | 2 | 10.5 | RT | Clear | Color/ppt | | | | | |
| $H_2O$ | 2 | 10.5 | 40° | Clear | Color | | | | | |
| $H_2O$ | 2 | 11.0 | RT | Clear | Color | | | | | |
| $H_2O$ | 2 | 11.0 | 40° | Clear | Color | | | | | |
| K-Phosphate 1.0M | 1.5 | 11 | RT | ppt | | | | | | |
| Na Acetate Buffer in D5W | 1 | 9.3 | RT | ppt | | | | | | |
| Na Acetate Buffer | 2 | 9.5 | RT | ppt | | | | | | |
| Na Acetate Buffer | 2 | 10.0 | RT | ppt | | | | | | |
| Na Acetate Buffer | 2 | 10.5 | RT | ppt | | | | | | |
| Na Acetate Buffer | 1 | 10.5 | RT | Clear | Clear | Clear | Clear | ppt | | |
| Na Acetate Buffer | 1 | 10.0 | RT | ppt | | | | | | |
| Na Acetate Buffer | 1 | 9.5 | RT | ppt | | | | | | |
| Na Acetate Buffer | 1 | 10.5 | RT | Clear | Clear | Clear | Clear | ppt | | |
| Na Acetate Buffer | 1 | 10.5 | 40° | Clear | Clear | Clear | Clear | ppt | | |
| Na Acetate Buffer | 1.0 with 88 mg β CD | 11 | RT | Clear | Clear | ppt | | | | |
| Na Acetate Buffer | 1.0 with 88 mg Encapcine | 11 | RT | Clear | ppt | ppt | | | | |
| Na Acetate Buffer | 1.0 with 88 mg β CD | 11 | RT | Clear | ppt | ppt | | | | |
| Na Acetate Buffer | 1.0 with 88 mg γ-CD | 11 | RT | Clear | ppt | | | | | |
| Na Acetate Buffer | 1.0 with 176 mg γ-CD | 9.8 | RT | Clear | Clear | ppt | | | | |
| Na Acetate Buffer | 1.0 with 440 mg γ-CD | 9.8 | RT | Clear | ppt | | | | | |

-continued

METOLAZONE SOLUBILITY

| Buffer Used (0.1M unless otherwise stated) | Final conc. Metolazone mg/ml (mg/ml) | Final pH of Solution | Temp. for Storage | 24 hr | 48 hr | 72 hr | 96 hr | 1 Wk | 2 Wk | 3 Wk |
|---|---|---|---|---|---|---|---|---|---|---|
| Buffer Na Acetate Buffer | 1.0 with 44 mg β-CD | 10.5 | RT | Clear | Clear | Clear | Clear | ppt | | |
| Na Acetate Buffer | 1.0 with 44 mg β CD | 10.5 | 40° | Clear | Clear | Clear | Clear | ppt | | |
| Na Acetate Buffer | 1.0 with 66 mg β CD | 10.0 | RT | Clear | Clear | Clear | Clear | ppt | | |
| Na Acetate Buffer | 1.0 with 66 mg β CD | 10.0 | 40° | Clear | Clear | Clear | Clear | ppt | | |
| Na Acetate Buffer 95% ETOH(3:1) | 3 | 3.4 | RT | ppt | | | | | | |
| Na Acetate Buffer | 1.5 | 11 | RT | ppt | | | | | | |
| Na Acetate | 1.0 with 30 mg PVP(MW 40,000) Int Visc 26–35 | 9.5 | RT | Clear ppt after 2–3 hrs | | | | | | |
| Na Acetate | 1.0 with 30 mg PVP(MW 40,000) Int Visc 28–32 | 9.5 | RT | Clear ppt after 2–3 hrs | | | | | | |
| Na Acetate | 1.0 with 30 mg PVP(MW 10,000) Int Visc 12–18 | 9.5 | RT | Clear ppt after 2–3 hrs | | | | | | |
| Na Acetate | 1.0 with 5 mg PCP (MW 40,000) Int Visc 26–35 | 9.5 | RT | Clear ppt 2–3 hrs | | | | | | |
| Na Acetate | 1.0 with 5 mg PVP (MW 40,000) Int Visc 28–32 | 9.5 | RT | Clear ppt 2–3 hrs | | | | | | |
| Na Acetate | 1.0 with 5 mg PVP (MW 10,000) Int Visc 12–18 | 9.5 | RT | Clear ppt 2–3 hrs | | | | | | |
| Saline | 1 | 10.5 | RT | Clear | Clear | Color | | | | |
| Saline | 1 | 10.5 | 40° | Clear | ppt | | | | | |
| Saline | 1 | 11.0 | RT | CLear | Color | | | | | |
| Saline | 1 | 11.0 | 40° | Clear | ppt | | | | | |
| Saline | 2 | 10.5 | RT | Clear | Color | | | | | |
| Saline | 2 | 10.5 | 40° | Clear | ppt | | | | | |
| Saline | 2 | 11.0 | RT | Clear | Clear | ppt | | | | |
| Saline | 2 | 11.0 | 40° | Clear | ppt | | | | | |
| Saline | 1 | 11.0 | RT | Clear | Color | | | | | |
| Saline | 1 | 11.0 | 40° | Clear | Color | | | | | |
| TAPS | 2 | 9.5 | RT | ppt | | | | | | |
| TAPS | 2 | 10.0 | RT | ppt | | | | | | |
| TAPS | 2 | 10.5 | RT | ppt | | | | | | |
| TAPS | 1.0 with 66 mg β CD | 10.0 | RT | Clear | Clear | ppt | | | | |
| TAPS 0.05 | 1 | 10.0 | RT | ppt | | | | | | |
| TAPS 0.05 | 1 | 11.5 | RT | Clear | Clear | Clear | Clear | Clear | ppt | |
| TAPS 0.05 | 1 | 11.5 | 40° | Clear | Clear | Clear | Clear | Clear | ppt | |
| TAPS 0.05 | 1 | 12.0 | RT | Clear | Clear | Clear | Clear | Clear | ppt | |
| TAPS 0.05 | 1 | 12.0 | 40° | Clear | Clear | Clear | Clear | Clear | ppt | |
| TAPS 0.05 | 2 | 11.5 | RT | Clear | ppt | | | | | |
| TAPS 0.05 | 2 | 11.5 | 40° | Clear | ppt | | | | | |
| TAPS 0.05 | 2 | 12.0 | RT | Clear | ppt | | | | | |
| TAPS 0.05 | 2 | 12.0 | 40° | Clear | ppt | | | | | |
| TEA | >1 | 10.5 | RT | ppt | | | | | | |
| TEA | >1 | 10.5 | 40° C. | ppt | | | | | | |
| TEA | >1 | 11.0 | RT | ppt | | | | | | |
| TEA | >1 | 11.0 | 40° C. | ppt | | | | | | |
| TEA | >1 | 11.5 | RT | ppt | | | | | | |
| TEA | >1 | 11.5 | 40° C. | ppt | | | | | | |
| TEA | 1.0 mg 66 mg β CD | 10.0 | RT | Clear | Clear | ppt | | | | |
| TEA + 1.8% NaCl(1:1) | >1 | 10.5 | RT | ppt | | | | | | |
| TEA + 1.8% NaCl(1:1) | >1 | 11.0 | RT | ppt | | | | | | |
| TEA + 1.8% NaCl(1:1) | >1 | 11.5 | RT | ppt | | | | | | |
| TEA + 1.8% | 2 | 9.5 | RT | ppt | | | | | | |

METOLAZONE SOLUBILITY

| Buffer Used (0.1M unless otherwise stated) | Final conc. Metolazone mg/ml (mg/ml) | Final pH of Solution | Temp. for Storage | Observations on stability after standing for period of time* | | | | | | |
|---|---|---|---|---|---|---|---|---|---|---|
| | | | | 24 hr | 48 hr | 72 hr | 96 hr | 1 Wk | 2 Wk | 3 Wk |
| TEA + 1.8% NaCl(1:1) | 2 | 10.0 | RT | ppt | | | | | | |
| TEA + 1.8% NaCl(1:1) | 2 | 10.5 | RT | ppt | | | | | | |
| TEA + 1.8% NaCl(1:1) | 1 | 10.0 | RT | ppt | | | | | | |
| TEA + 1.8% NaCl(1:1) | 1 | 11.5 | RT | Clear | Clear | ppt | | | | |
| TEA + 1.8% NaCl(1:1) | 1 | 11.5 | 40° | Clear | ppt | | | | | |
| TEA + 1.8% NaCl(1:1) | 1 | 12.0 | RT | Clear | ppt | | | | | |
| TEA + 1.8% NaCl(1:1) | 1 | 12.0 | 40° | Clear | ppt | | | | | |
| TEA + 1.8% NaCl(1:1) | 2 | 11.5 | RT | Clear | ppt | | | | | |
| TEA + 1.8% NaCl(1:1) | 2 | 11.5 | 40° | Clear | ppt | | | | | |
| TEA + 1.8% NaCl(1:1) | 2 | 12.0 | RT | Clear | ppt | | | | | |
| TEA + 1.8% NaCl(1:1) | 2 | 12.0 | 40° | Clear | ppt | | | | | |
| Tricine[6] | 1 | 11.3 | RT | ppt | | | | | | |
| Tricine | 1 | 11.0 | RT | ppt | | | | | | |
| Tricine | 1 | 10.4 | RT | ppt | | | | | | |
| Tricine | 1.5 | 10.4 | RT | ppt | | | | | | |
| Tricine | 2 | 9.5 | RT | ppt | | | | | | |
| Tricine | 2 | 10.0 | RT | ppt | | | | | | |
| Tricine | 2 | 10.5 | RT | ppt | | | | | | |
| Tricine | 1 | 10.0 | RT | ppt | | | | | | |
| Tricine | 1.0 with 66 mg β CD | 10.0 | RT | Clear | Clear | ppt | | | | |
| Tricine 0.05 | 1 | 11.5 | RT | Clear | Clear | Clear | Clear | Clear | Clear | ppt |
| Tricine 0.05 | 1 | 11.5 | 40° | Clear | ppt | | | | | |
| Tricine 0.05 | 1 | 12.0 | RT | Clear | Clear | Clear | Clear | Clear | Clear | ppt |
| Tricine 0.05 | 1 | 12.0 | 40° | Clear | ppt | | | | | |
| Tricine 0.05 | 2.0 | 11.5 | RT | Clear | Clear | Clear | Clear | Clear | ppt | |
| Tricine 0.05 | 2.0 | 11.5 | 40° | Clear | Clear | Clear | Clear | Clear | ppt | |
| Tricine 0.05 | 2.0 | 12.0 | RT | Clear | Clear | Clear | Clear | Clear | ppt | |
| Tricine 0.05 | 2.0 | 12.0 | 40° | Clear | Clear | Clear | Clear | Clear | ppt | |
| TEA | 1 | 11.3 | RT | ppt | | | | | | |
| TEA | 1 | 10.9 | RT | ppt | | | | | | |
| TEA | 1 | 10.6 | RT | ppt | | | | | | |
| TEA | 2 | 9.5 | RT | ppt | | | | | | |
| TEA | 2 | 10.0 | RT | ppt | | | | | | |
| TEA | 2 | 10.5 | RT | ppt | | | | | | |
| TEA | 1 | 10.0 | RT | ppt | | | | | | |
| TEA | 1.5 | 10.4 | RT | ppt | | | | | | |
| Tris | 1.5 | 10.4 | RT | ppt | | | | | | |
| Tris | 1.5 | 7.5 | RT | ppt | | | | | | |
| Tris | 1.5 | 10.4 | RT | ppt | | | | | | |
| Tris | 1.5 | 10.1 | RT | ppt | | | | | | |
| Tris | 2 | 10.8 | RT | ppt | | | | | | |
| Tris | 5 | 11.2 | RT | ppt | | | | | | |
| Tris | 10 | 12 | RT | ppt | | | | | | |
| Tris | 2 | 9.5 | RT | ppt | | | | | | |
| Tris | 2 | 10.0 | RT | ppt | | | | | | |
| Tris | 2 | 10.5 | RT | ppt | | | | | | |
| Tris | 1 | 10.0 | RT | ppt | | | | | | |
| Tris | 1.0 with 66 mg β CD | 10.0 | RT | Clear | Clear | ppt | | | | |

[1]3O[(1,1-dimethyl-2-hydroxyethyl)amino]-2-hydroxypropanesulfonic acid.
[2]N,N-bis-(2-hydroxyethyl)glycine
[3]3-(cyclohexylamino)propanesulfonic acid
[4]2-(cyclohexylamino)ethanesulfonic acid
[5]3-([tris-hydroxymethyl)methyl]amino)propanesulfonic acid
[6]N-[tris-hydroxymethyl)methyl]glycine GRAPHIC CODES
RT = Room Temperature
CD = Cyclodextrin
PVP = Polyvinlypyrrolidone
*Solutions remained colorless unless indicated otherwise As these data demonstrate, Metolazone is unexpectedly stable as a formulation in 0.05M Bis-Tris at pHs from about 11.5 to 12.0.

EXAMPLE 2

Metolazone Rat Experiment

Rats 450 gms received 2 mg/kg Metolazone intrapertioneally in tris buffer. Group I Control received Bis-Tris containing no metolazone, Group II received 1 ml of a solution containing 1 mg/ml metolazone in 0.05M Bis-Tris at pH 11.5 to 12. Metolazone and Group III are control animals receiving Metolazone on a different day. The volume of urine produced by the rats is shown below.

| Control | Metolazone 2 mg/kg |
|---|---|
| 8 | 16 |
| 7 | 15 |
| 9 | 17 |
| 10 | 18 |
| 10 | 17 |
| 9 ± 1 | 17 ± 1 |

From the foregoing it will be appreciated that, although specific embodiments of the invention have been described herein for purposes of illustration, various modifications may be made without deviating from the spirit and scope of the invention.

What is claimed is:

1. A solution suitable for parenteral administration comprising about 1.0 to 2.0 mg/ml of a compound of the formula

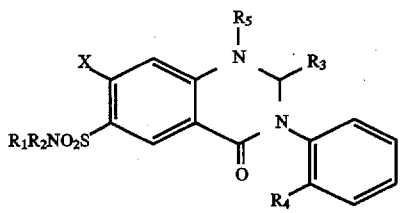

wherein X is halogen;

$R_1$, $R_2$, $R_3$, $R_4$ are independently selected from hydrogen and alkyl having from 1 to 6 carbon atoms; and $R_5$ is hydrogen or alkyl having from 1 to 6 carbon atoms, dissolved in an aqueous about 0.05M Bis-Tris buffer system having a pH of from about 11.5 to 12.0.

2. A solution suitable for parenteral administration according to claim 1 wherein the compound is metolazone.

3. A method for the treatment of a patient suffering from hypertension which comprises the intravenous administration of an effective amount of a solution according to claim 2.

4. A solution comprising an effective diuretic amount of a mixture of furosemide and about 1.0 to 2.0 mg/ml metolazone in an aqueous about 0.05M Bis-Tris buffer at a pH of from about 11.5 to 12.

* * * * *